US011872393B2

(12) United States Patent
Rump

(10) Patent No.: US 11,872,393 B2
(45) Date of Patent: Jan. 16, 2024

(54) IMPLANTABLE ELECTRODE WITH A STUB LINE

(71) Applicant: BIOTRONIK SE & Co. KG, Berlin (DE)

(72) Inventor: Jens Rump, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 75 days.

(21) Appl. No.: 16/782,141

(22) Filed: Feb. 5, 2020

(65) Prior Publication Data

US 2020/0254235 A1 Aug. 13, 2020

(30) Foreign Application Priority Data

Feb. 13, 2019 (DE) .................... 10 2019 103 612.7

(51) Int. Cl.
*A61N 1/05* (2006.01)
*A61N 1/36* (2006.01)
*A61N 1/08* (2006.01)
*A61N 1/37* (2006.01)

(52) U.S. Cl.
CPC ....... *A61N 1/0551* (2013.01); *A61N 1/36062* (2017.08); *A61N 1/086* (2017.08); *A61N 1/37* (2013.01); *A61N 1/3718* (2013.01)

(58) Field of Classification Search
CPC .. A61N 1/0551; A61N 1/36062; A61N 1/086; A61N 1/3718; A61N 1/37
See application file for complete search history.

(56) References Cited

U.S. PATENT DOCUMENTS

| | | | | |
|---|---|---|---|---|
| 5,217,010 A | * | 6/1993 | Tsitlik | A61N 1/36042 607/9 |
| 5,683,434 A | * | 11/1997 | Archer | A61N 1/3754 607/36 |
| 2003/0144719 A1 | * | 7/2003 | Zeijlemaker | A61N 1/05 607/122 |
| 2005/0090886 A1 | * | 4/2005 | MacDonald | A61N 1/086 607/122 |

(Continued)

FOREIGN PATENT DOCUMENTS

| | | |
|---|---|---|
| EP | 1923094 A1 | 5/2008 |
| EP | 2465570 A1 | 6/2012 |
| EP | 2667929 B1 | 6/2018 |

OTHER PUBLICATIONS

German Search Report for German Case No. DE 10 2019 103 612.7, dated Oct. 7, 2019 (7 pages).

(Continued)

Primary Examiner — Pamela M. Bays
(74) Attorney, Agent, or Firm — Buchanan Ingersoll & Rooney PC

(57) ABSTRACT

An implantable electrode includes an outer tube, which has a distal end and a proximal end, wherein the implantable electrode is connectable in the region of the proximal end to an active device. At least one electrode line is arranged in the outer tube. At least one electrode pole, which is electrically connected to the at least one electrode line, for electrically contacting tissue surrounding the electrode in the implanted state of the electrode is arranged in the region of the distal end. A stub line for extending the electrical length of the at least one electrode line is connected to the at least one electrode line in the region of the distal end or the proximal end.

20 Claims, 9 Drawing Sheets

(56) References Cited

U.S. PATENT DOCUMENTS

| | | | |
|---|---|---|---|
| 2008/0243218 A1* | 10/2008 | Bottomley | A61N 1/05 607/116 |
| 2009/0240296 A1* | 9/2009 | Zeijlemaker | A61N 1/37 607/5 |
| 2009/0259281 A1 | 10/2009 | Weiss et al. | |
| 2010/0023000 A1* | 1/2010 | Stevenson | A61B 18/1492 606/33 |
| 2010/0168821 A1* | 7/2010 | Johnson | A61B 18/1492 607/63 |
| 2010/0211129 A1* | 8/2010 | Goedeke | A61N 1/37 607/9 |
| 2011/0093054 A1* | 4/2011 | Ameri | A61N 1/05 607/122 |
| 2012/0109261 A1* | 5/2012 | Stancer | A61N 1/3718 607/60 |
| 2013/0226266 A1* | 8/2013 | Murtonen | A61N 1/378 607/62 |
| 2015/0170792 A1 | 6/2015 | Alford et al. | |
| 2016/0331960 A1 | 11/2016 | Katnani et al. | |

OTHER PUBLICATIONS

German Search Report for German Case No. DE 10 2020 100 121.5, dated Sep. 17, 2020 (8 pages).

\* cited by examiner

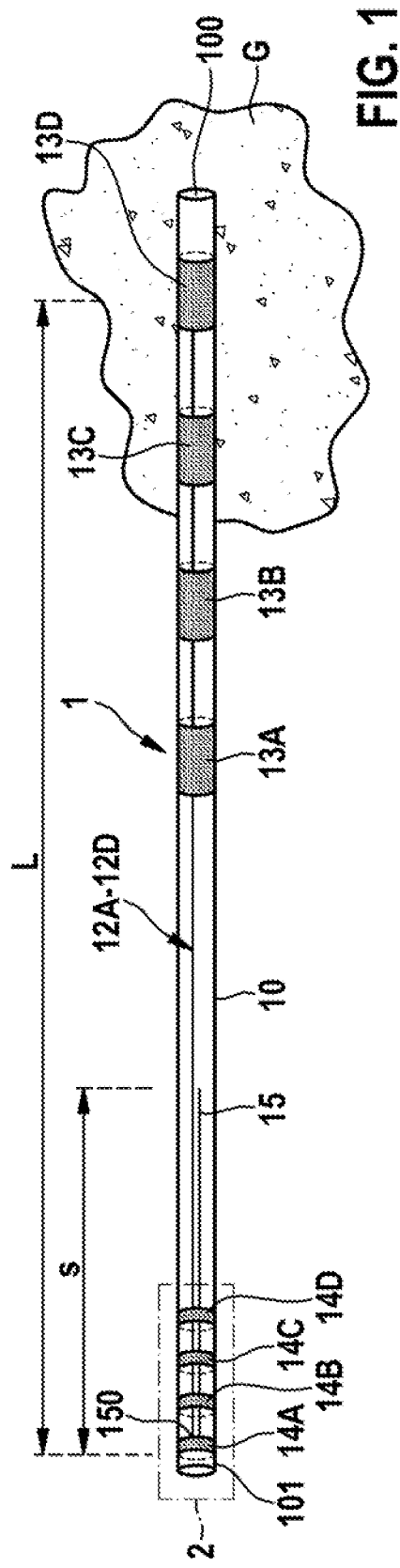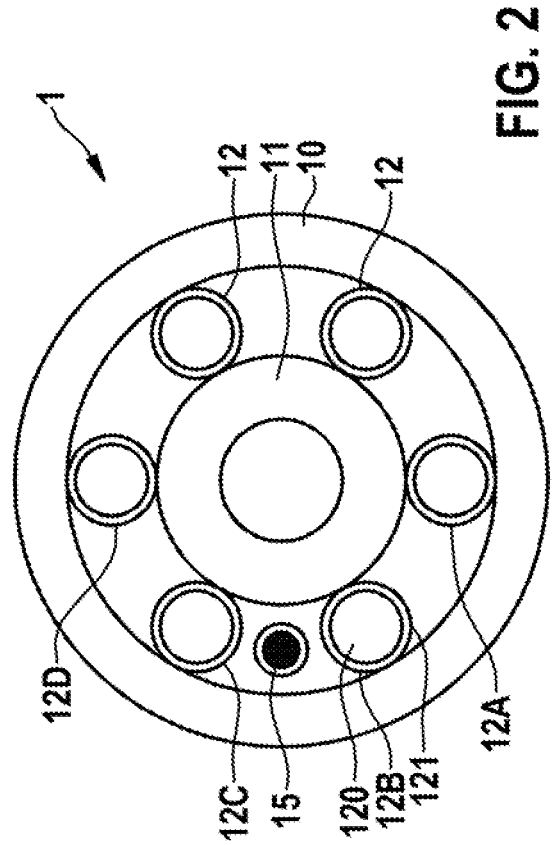

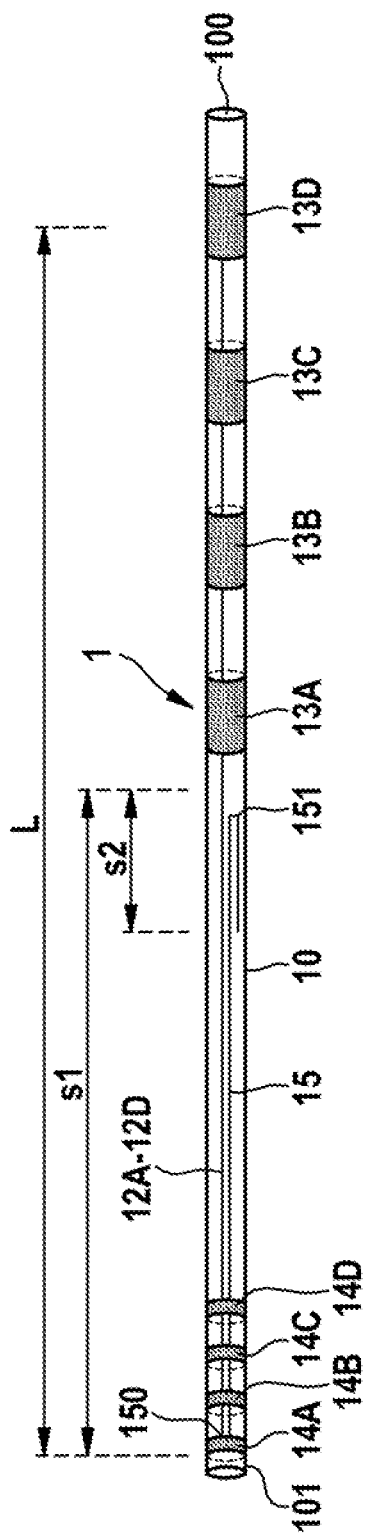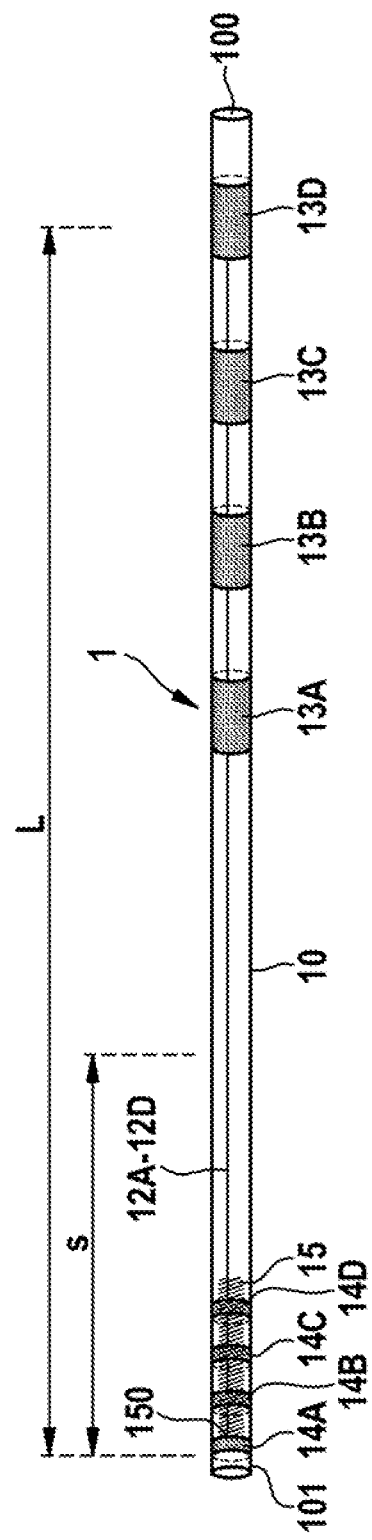

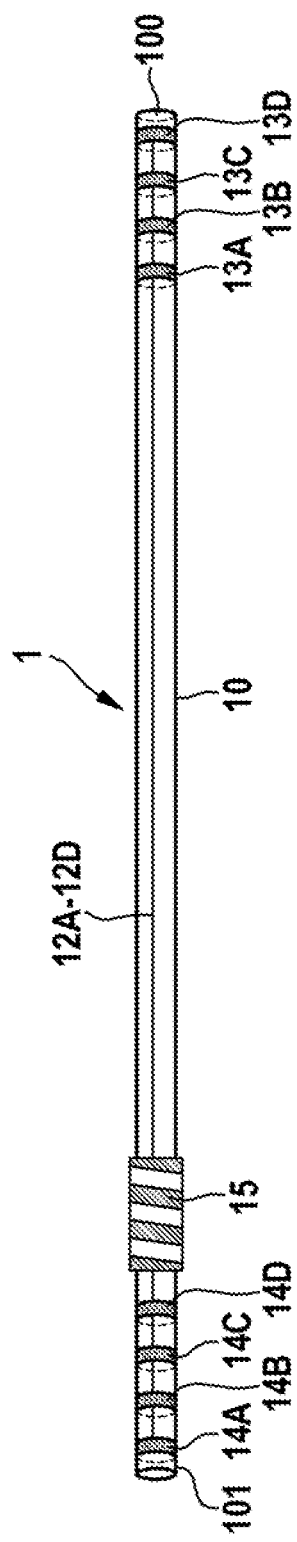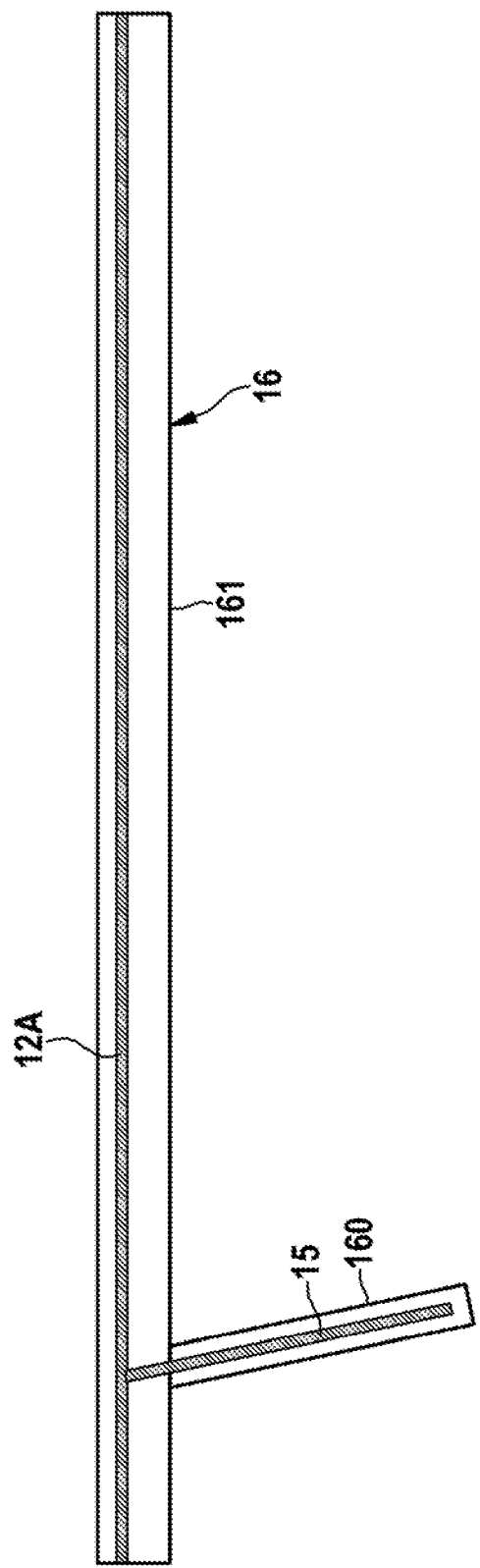

IMPLANTABLE ELECTRODE WITH A STUB LINE

CROSS REFERENCE TO RELATED APPLICATIONS

This patent application claims the benefit of and priority to co-pending German Patent Application No. DE 10 2019 103 612.7, filed on Feb. 13, 2019 in the German Patent Office, which is hereby incorporated by reference in its entirety.

TECHNICAL FIELD

The present invention relates to an implantable electrode according to the preamble of claim 1 and to a system comprising an implantable electrode.

BACKGROUND

An implantable electrode of this kind may be connected to an active electrical device, for example, a cardiac pacemaker or a neuro-stimulator and, for example, may be implanted in the form of a heart electrode in the heart or in the form of a neuro electrode on the spinal cord, on the vagus nerve or also in the brain of a patient. Electrical signals for stimulation may be delivered to the patient via such an electrode and an active device connected thereto.

Such an implantable electrode comprises an outer tube, which has a distal end and a proximal end, wherein the implantable electrode is connectable in the region of the proximal end to an associated active device. The implantable electrode comprises at least one electrode line arranged in the outer tube and at least one electrode pole, which is arranged in the region of the distal end and is electrically connected to the at least one electrode line, for electrically contacting tissue surrounding the electrode when the electrode is in the implanted state.

Such an electrode, following its implantation, remains in the body of the patient for a relatively long period of time. Such an electrode should allow the possibility for examinations to be performed on the patient during this time, in particular MRT (magnetic resonance tomography) examinations, meaning that an electromagnetic field generated during an MRT examination must not heat up the electrode, as this could be harmful to the patient.

An electrode implanted in a patient might be heated in some circumstances by the in-coupling of electromagnetic fields. The coupling of the electrode to the electromagnetic field of an MR tomograph (which generates an excitation field with an excitation frequency dependent on the magnetic field strength, for example, at approximately 64 MHz at 1.5 Tesla) is dependent here on the effective line length of the electrode lines of the electrode. If the effective line length of the electrode is in the range of a (series) resonance frequency of the electromagnetic field, electromagnetic fields may thus be coupled into the electrode and may cause the electrode to heat up, which should be avoided where possible.

An electrode, in particular for neuro-stimulation, should be made in a thin design. In addition, there are specifications with regard to the length of the electrode line and the maximum ohmic resistance.

An implantable electrode which has a first, inner conductor and an outer conductor which runs outside the inner conductor is known from U.S. Publication No. 2009/0259281.

An implantable medical electrode in which a fiber contains physical changes which define a plurality of radiofrequency reflection points which are situated along the length of the fiber is known from European Patent No. 2 667 929.

In an electrode device known front U.S. Publication No. 2015/0170792, conductors are arranged helically. In this case an inner conductor is electrically contacted with an electrode pole.

The present invention is directed at overcoming one or more of the above-mentioned problems.

SUMMARY

An object of the present invention is to provide an implantable electrode and also a system comprising such an implantable electrode, wherein the implantable electrode has one or more electrode lines, however electrical heating at a predetermined MR excitation frequency within the scope of an MRI examination is prevented.

At least this object is achieved by a subject having the features of claim 1.

Thus, the implantable electrode comprises a stub line, which is connected in the region of the distal end or the proximal end to the at least one electrode line in order to extend the electrical length of the at least one electrode line.

The implantable electrode has an outer tube which, for example, is manufactured from an electrically insulating material, for example, a silicone or polyurethane material, and encases one or more electrode lines. Electrode lines run lengthwise in the outer tube and are connected at the distal end of the outer tube to electrode poles which are accessible from outside in such a way that the electrode poles may electrically contact surrounding tissue when the electrode is implanted in a patient. By contrast, at the proximal end of the outer tube, the electrode lines are electrically contacted with the active device when the electrode is connected to an associated, active electrical device, and therefore electrical signals may be fed from the active device into the electrode lines and may be delivered to the patient via the electrode poles.

Such an active device may be configured, for example, as a cardiac pacemaker, CRT dev ice, defibrillator, or also as an electrophysiology device. In this case, the electrode—as a heart electrode—shall be implanted in particular in the heart of a patient. However, the electrode may also be used in the form of a neuro electrode for neuro-stimulation at the spinal cord, at the vagus nerve or in the brain (what is known as spinal-cord stimulation (SCS), vagus nerve stimulation (VNS) or deep brain stimulation (DBS)).

In the implanted position, the electrode lies with its electrode poles against a stimulation site in the patient, for example, in the region of the human heart or in the region of the spinal cord. The active device, as implantable device, likewise may be implanted in the patient (for example, in the form of a cardiac pacemaker or neuro-stimulator). However, the active device may also be situated outside the patient.

In order to reduce an electromagnetic excitation of the implanted electrode within the scope of an MRI examination on account of an electromagnetic MR excitation field being coupled into the electrode, and thus in order to reduce excessive heating of the electrode, particularly at the electrode poles, the at least one electrode line of the electrode is connected to a stub line, which modifies the effective line length of the at least one electrode line in such a way that a resonant excitation at the at least one electrode line is inhibited. The stub line is electrically connected in the region of the distal end or the proximal end to the at least one electrode line, wherein it is also conceivable and possible that a first stub line is electrically connected in the region of the distal end to the at least one electrode line and a second stub line is electrically connected in the region of the proximal end to the at least one electrode line, such that the effective line length of the at least one electrode line is modified by being extended on both sides, via one stub line in each case.

The stub line is electrically connected at one of its ends to the associated electrode line. The other end of the stub line, by contrast, is free.

The at least one electrode line has a mechanical electrode line length, whereas the stub line runs with a mechanical stub line length in the outer tube. The line length of the at least one electrode line is given here from the sum of the electrode line length and the stub line length and is additionally influenced by the terminating impedance of the at least one electrode line at the proximal end and the distal end, that is to say on the side of an active device connected to the electrode and on the side of the at least one electric pole and therefore the electrical coupling to surrounding tissue.

In principle, the in-coupling of an electromagnetic field at a predetermined MR excitation frequency—for example, approximately 64 MHz at an MR magnetic field strength of 1.5 Tesla and approximately 123 MHz at an MR magnetic field strength of 3 Tesla—into the at least one electrode line is maximal with an effective line length corresponding to a series resonance. At such a series resonance, the value of the impedance is minimal, and on account of maximal in-coupling of the electromagnetic field there may be a field magnification and therefore a comparatively high heating of the at least one electrode line, predominantly at an electrode pole connected to the electrode line. With an effective line length of the at least one electrode line, corresponding to a parallel resonance, the value of the impedance at the at least one electrode line is, by contrast, maximal, and accordingly the in-coupling of the electromagnetic field is eliminated. It is thus desirable to set the effective line length of the at least one electrode line such that it corresponds to a parallel resonance.

It should be noted at this juncture that the excitation frequency of the 3 Tesla MR tomographs, which are currently customary, is 123 MHz, since in these devices the coils generating the sialic magnetic field generate a magnetic field of just about 2.9 Tesla. At a magnetic field strength of 3.0 Tesla this excitation frequency is 128 MHz. For this reason, an excitation frequency of 123 MHz is specified hereinafter for 3-Tesla tomographs.

It is possible to determine when a parallel resonance occurs at a predetermined MR excitation frequency, for example 64 MHz or 123 MHz, by computer simulations or also by way of measurements on the basis of suitable test series. For example, the impedance spectrum for different line lengths may be determined by way of measurements on the basis of the reflection coefficient of the at least one electrode line with simulation of human tissue by a saline solution. From this, at the predetermined MR excitation frequency, an advantageous effective line length at the at least one electrode line corresponding to a parallel resonance may be determined. On the basis of this effective line length thus determined, the length of the stub line may then be selected such that the sum of the stub line length and the electrode line length of the at least one electrode line corresponds to the desired effective line length. If the at least one electrode line, for example, is 550 mm long, and should the effective line length formed from electrode line and stub line correspond to 600 mm for a parallel resonance at for example 64 MHz, the stub line length should be selected to be 50 mm.

The effective line length may be coordinated here with a first parallel resonance in the impedance spectrum. However, it is also conceivable and possible to coordinate tire effective line length to a parallel resonance of higher order by extending the stub line length by half a wavelength (or a multiple of a half wavelength).

The stub line is connected at the distal end or at the proximal end to the at least one electrode line. Here, the stub line may be formed in different ways and, in particular, may run in a straight line parallel to the at least one electrode line in the outer tube, helically around the at least one electrode line within the outer tube, or also in a meandering fashion.

If the stub line runs in a straight line, the stub line, for example, runs from the distal end in the direction of the proximal end over such a length that the sum of die stub line length and the electrode line length corresponds to the desired length for an effective line length at parallel resonance. The stub line may also run firstly away from one particular end (for example, the distal end) in die direction of the other end, and may be reversed through 180° at a turning point, such that the stub line runs from the turning point back in the direction of the original end, for example the distal end. The stub line may in this way run in a straight line in some sections, but may be reversed at one or more turning points and thus may run back and forth.

If the stub line runs helically, the stub line thus has a helix shape, which is encased inside die outer tube and preferably surrounds the at least one electrode line. By way of such a helix shape, a stub line of comparatively great mechanical length may be provided over a comparatively small axial length of extent.

If the stub line runs in a meandering fashion, the stub line, for example, thus forms portions along a plane which run in a meandering fashion relative to one another and thus form a meander shape. Again, a stub line of comparatively great mechanical length may be provided over a comparatively small axial length of extent.

The stub line, in one embodiment, for example may be formed by flexible conductive track. Such a flexible conductive track, for example, may be applied to a support, for example, printed on, wherein the support for example consists of an electrically insulating film material, for example, what is known as an LCP (liquid crystal polymer) film, and is thus flexible.

By means of such a flexible conductive track, a helical or meandering stub line may be realized, for example Such a flexible conductive track may be laid, for example, in wound form, in the outer tube in order to form the helix shape. A meandering conductive track may be applied, for example, to a flat support, for example, printed on.

In one embodiment, the stub line is arranged jointly with the at least one electrode line on a support, for example, primed on a support. The electrode line may thus also be realized by a flexible conductive track on a support, which enables simple manufacture of the at least one electrode line together with the electrically attached stub line.

If the stub line and the at least one electrode line are arranged jointly on a support, the stub line and the at least one electrode line, for example, may thus run jointly over a surface of the support. The stub line and the at least one electrode line in this case are formed on the support along the same plane. Alternatively, however, a multi-layer structure is also possible, in which the stub line and the at least one electrode line arc formed by conductive tracks on the support running parallel to one another along different planes. The stub line or the at least one electrode line may be formed here, for example, on a surface of the support, whereas the other line is embedded in the support. For example, the stub line may be formed in a meandering fashion on a surface of the support, whereas the at least one electrode line is embedded in the support in another plane or is arranged on the other side of the support. However, it is also conceivable and possible that both the stub line and the at least one electrode line are embedded in the support, but run in the support in different planes.

In one embodiment, the implantable electrode has a plurality of electrode lines and a plurality of electrode poles arranged in the region of tire distal end. Here, each electrode line is connected to an associated electrode pole, so that electrical signals may be conducted via the electrode line to the associated electrode pole and may be delivered via the electrode pole into the surrounding tissue (in the case of an implanted electrode). Here, for example, the electrode poles are each formed as a sleeve at the distal end of the outer tube and are accessible from outside, so that surrounding tissue may be electrically contacted by the electrode poles. The electrode poles of the different electrode lines are offset here in relation to one another axially along the direction of longitudinal extent of the electrode in that adjacent electrode poles are distanced from one another, for example, by a predetermined spacing, for example, between 2 mm and 10 mm, for example, 5 mm.

If a plurality of electrode poles are provided, precisely one stub line is connected to the plurality of electrode lines at the distal end or at the proximal end. At the relevant end, the plurality of electrode lines are thus connected merely to one single stub line, wherein it may also be provided that (precisely) one stub line is provided at each of the distal end and also the proximal end. The stub line at the relevant end is used here to modify the effective line length of all electrode lines so that an electromagnetic field at a predetermined MR excitation frequency may be coupled into the electrode lines only with difficulty.

In order to modify the effective line length of all electrode lines by a common stub line such that the effective line length corresponds preferably to a parallel resonance, the electrode lines are preferably electrically short-circuited in the region of the relevant end, that is to say in the region of the distal end or the proximal end, at the predetermined MR excitation frequency, that is to say, for example, 64 MHz or 123 MHz. To this end, for example, capacitors, for example, in the form of separate capacitor elements, may act between the electrode lines and cause an effective electrical short circuit at the MR excitation frequency, so that a stub line which is electrically connected to one of the electrode lines is also electrically connected to the other electrode lines by way of the short-circuit. An individual stub line is therefore sufficient to modify the effective line length at all electrode lines in a desirable manner.

By contrast, the electrode lines are effectively not short-circuited for the low-frequency electrical signals to be delivered via the electrode poles. Such signals are of a much lower frequency than the MR excitation frequency, and therefore the electrode lines for the stimulation signals are effectively electrically separated from one another.

Whereas the electrode poles are arranged in the region of the distal end in order to be electrically coupled to the surrounding tissue when the electrode is implanted, the electrode, in one embodiment, has connection elements at the proximal end, for example, in the form of sleeve-shaped electrical contacts, which are used to electrically contact the active device. The electrode, for example, may be connectable to the active dev ice by plugging via a suitable plug-in connector. In the connected position, the connection elements contact associated electrical contacts of the active device, and therefore an electrical connection is established between the active device and the electrode, in particular the electrode lines of the electrode.

In a particular embodiment of the implantable electrode, the electrode n comprises n (n=2 to 16) electric lines, n electrode poles in the region of the distal end of the electrode so as to be electrically coupled to the surrounding tissue when the electrode has been implanted, and n connection elements at the proximal end of the electrode for electrically contacting the electrode with the active device. Each of the n electrode poles is connected here to the associated electrode line. Furthermore, each of the n connection elements is connected to the associated electrode line. Here, each of the n connection elements is associated with one of the n electrode poles, wherein the connection element is electrically conductively connected to the associated electrode pole by one of the n electrode lines. Furthermore, the number 11 of electrode lines, electrode poles and connection elements lies in the range between 4 and 12, and more preferably in the range between 6 and 10, and more preferably the number n of electrode lines, electrode poles and connection elements is 8.

In a further embodiment, the electrode of the above-described type is designed to carry out spinal cord stimulation (SCS) via the electrode poles of the one electrode.

A system comprises an active device and an electrode of the above-described kind connected to the active device. Such an active device may have, for example, a housing and at least one electrical contact element for electrically contacting the at least one electrode line of the electrode. In the connected position, the electrode is, for example, contacted via connection elements associated with the electrode lines to electrical contacts of the active device, so that in this way an electrical connection is established between the active device and the electrode.

Each electrical contact element of the active device may be electrically short-circuited here to the housing at a predetermined M R excitation frequency, for example, via capacitors in the form of separate capacitor elements. In this case, the electrode lines on the side of the active device—at the MR excitation frequency—are connected with a terminating impedance in the form of a short circuit. With arrangement of a stub line at the proximal end, this makes it possible to dispense with capacitors within the electrode for short-circuiting of the electrode lines, wherein just one stub line, however, is sufficient to extend the effective line length of all electrode lines.

In a further embodiment, the system comprises an active device and two electrodes of the above-described kind connected to the active device.

In a further embodiment, the system consisting of the active device and the at least one electrode of the above-described kind is designed to provide spinal cord stimulation (SCS) via the electrode poles of the at least one electrode.

In a further embodiment, the system for spinal cord stimulation comprises two electrodes of the above-described kind.

Additional features, aspects, objects, advantages, and possible applications of the present invention will become apparent from a study of the exemplary embodiments and examples described below, in combination with the Figures, and the appended claims.

DESCRIPTION OF THE DRAWINGS

The concept forming the basis of the present invention will be explained in greater detail hereinafter with reference to the exemplary embodiments shown in the Figures, in which:

FIG. 1 shows a view of an exemplary embodiment of an electrode with electrode lines and a stub line encased in an outer tube;

FIG. 2 shows a schematic cross-sectional view through air electrode;

FIG. 7 shows a view of another exemplary embodiment of an electrode with a stub line;

FIG. 8 shows a view of another exemplary embodiment of an electrode with a stub line;

FIG. 10A shows a view of another exemplary embodiment of an electrode with a stub line;

FIG. 10B shows a separate view of the stub line together with an associated electrode line;

DETAILED DESCRIPTION

Figure 3:
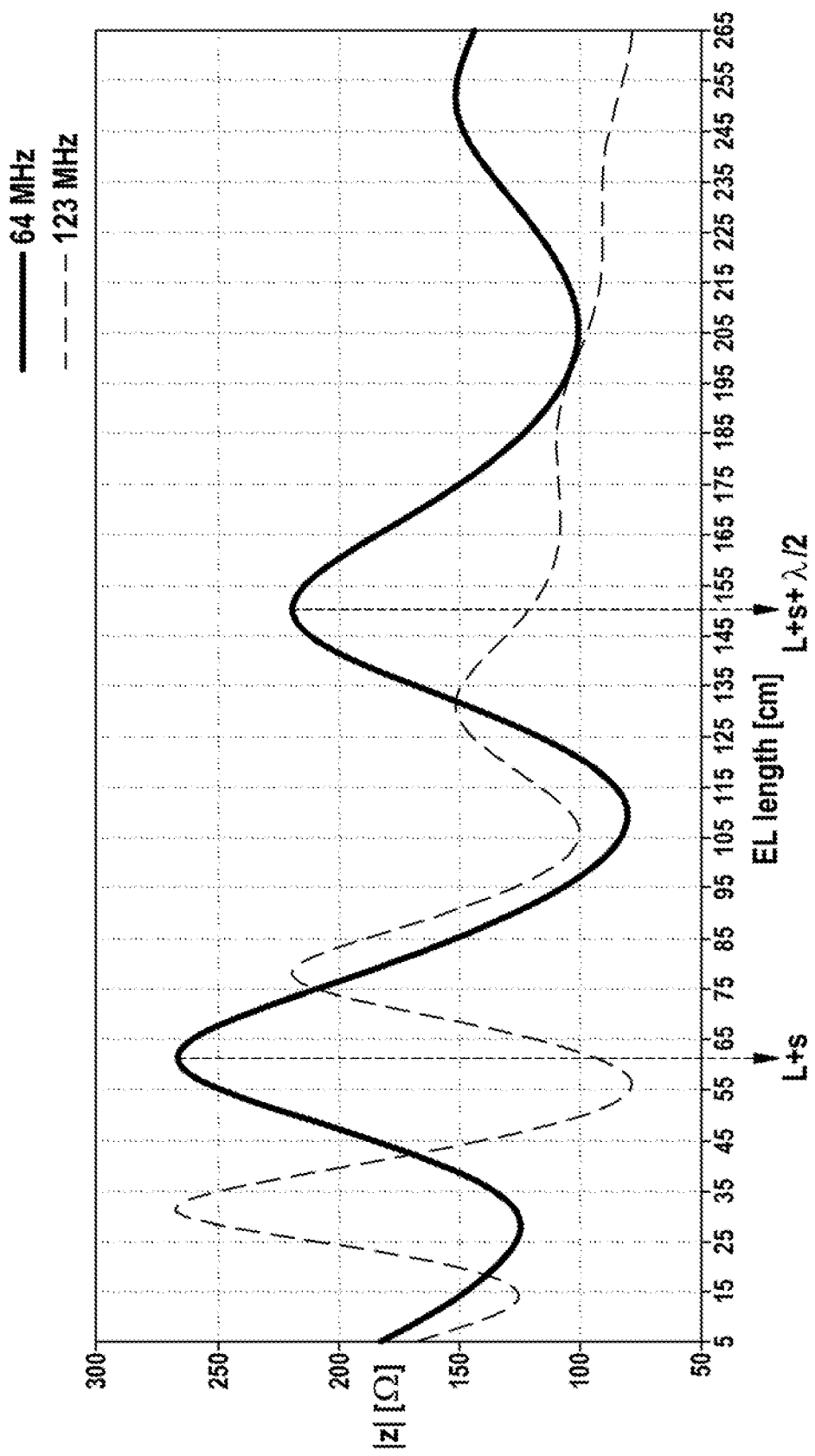
FIG. 3 shows an exemplary view of an impedance spectrum for two different MR excitation frequencies.

An electrode 1 shown by way of example in FIG. 1 on the basis of an exemplary embodiment has an outer tube 10, which is manufactured from electrically insulating material, for example, a silicone or polyurethane material and runs lengthwise along a direction of longitudinal extent. The electrode 1 has a plurality of electrode lines 12A-12D, which run within the outer tube 10 between a proximal end 101 of the outer tube 10 and a distal end 100 of the outer tube 10 and are used to conduct electrical signals from an active device to two electrode poles 13A-13D at the distal end 100.

The electrode poles 13A-13D are arranged axially offset in relation to one another in the region of the distal end 100 of the outer tube 10 of the electrode 1. The electrode poles 13A-13D are sleeve-shaped and are accessible from outside in such a way that surrounding tissue G in an implanted position of the electrode 1 may be electrically contacted via the electrode poles 13A-13D, and therefore excitation signals may be delivered into the tissue G. Each electrode pole 13A-13D is connected here to an associated electrode line 12A-12D.

At the proximal end 101, the electrode 1 has connection elements 14A-14D, which are sleeve-shaped and are used to electrically contact the active device 2. The active device 2 feeds electrical signals via the connection elements 14A-14D into the electrode lines 12A-12D, which conduct these signals to the electrode poles 13A-13D and thus deliver them into the tissue G.

A basic, exemplary structure of such an electrode 1 is shown in FIG. 2 in cross-section perpendicularly to the direction of longitudinal extent. The outer tube 10 forms an outer sleeve of die electrode 1 and encases the electrode lines 12, 12A-12D encased therein. The electrode lines 12, 12A-12D are grouped here around an inner tube 11 and each has an inner conductor 120 and a surrounding electrical insulation 121 so that the electrode lines 12, 12A-12D are each electrically insulated.

The space in FIG. 2 formed by the outer tube 10 and the inner tube 11, which space contains the electrode lines 12, 12A-12D, may be filled with an insulating material so that the electrode lines 12, 12A-12D are each electrically insulated. The electrode lines 12, 12A-12D are thus surrounded by a continuous surrounding electrical insulation 121.

The electrode 1 may have one or more electrode lines 12, 12A-12D, for example, three, four, five or six electrode lines 12, 12A-12D.

The outer tube 10 may, for example, have an outer diameter between 1 mm and 1.5 mm. The inner diameter of the inner tube 11 may be, for example, between 0.3 mm and 0.5 mm.

Such an electrode 1 may be used, for example, as a heart electrode for implantation in the human heart. However, such an electrode 1 may also be formed as a neuro electrode and thus may be implanted into the spinal cord or into the brain of a patient.

In the case of use as a heart electrode, the active device 2 may be embodied, for example, as a cardiac pacemaker, CRT device, defibrillator, or electrophysiology device, for example, for catheter ablation. The active device 2, in one embodiment, likewise may be implanted. Alternatively, die active device 2 may also be operated outside the human body, and therefore may be connected to the electrode 1 outside the human body.

In the case of use as a neuro electrode, the active device 2 is designed for neuro-stimulation in the spinal cord or in the human brain (what is known as spinal-cord stimulation (SCS) or deep brain stimulation (DBS)).

Also, in the case of an implanted electrode 1, medical examinations should be possible on the patient without limitation, in particular also an MRI examination, if necessary even within the scope of the implantation for verification of the position of the electrode 1. Here, excess heating on account of an in-coupling of an electromagnetic field at the electrode poles within the scope of the MRI examination should be avoided in order to rule out injury to the patient.

The electrode lines 12A-12D, as shown in FIG. 1, run over an electrode line length L within the outer tube 10, wherein the mechanical length of the individual electrode lines 12A-12D may differ slightly from one another depending on the axial position of the electrode poles 13A-13D. The possibility of electromagnetic fields being coupled in is dependent fundamentally on the effective line length of the electrode lines 12A-12D, wherein in principle there is increased in-coupling at a series resonance, but by contrast an in-coupling is substantially eliminated in the case of a parallel resonance.

FIG. 3 shows—by way of example—impedance spectra for an MR excitation frequency of 64 MHz (corresponding to a magnetic field strength of 1.5 Tesla, solid line in FIG. 3) and an MR excitation frequency of 123 MHz (corresponding to a magnetic field strength of 2.9 Tesla, dashed line in FIG. 3). Minima in each of the curves of the spectrum correspond to series resonances, whereas maxima correspond to parallel resonances.

It may be seen from FIG. 3 that for an MR excitation frequency of 64 MHz a first parallel resonance is present at an effective line length of approximately 60 cm. A second parallel resonance occurs at an effective line length of approximately 150 cm.

It may be seen from FIG. 3 that for an MR excitation frequency of 123 MHz a first parallel resonance is present at an effective line length of approximately 30 cm. A second parallel resonance occurs at an effective line length of approximately 80 cm. A third parallel resonance occurs at an effective line length of approximately 130 cm.

It may be derived from this that the effective line length of the electrode lines 12A-12B should be optimized to a length that corresponds (approximately) to a parallel resonance, that is to say, for example, 60 cm at 64 MHz or 80 cm at 123 MHz.

In the exemplary embodiment according to FIG. 1, a stub line 15 is provided in order to modify the effective line length of the electrode lines 12A-12D and is electrically connected to one of the electrode lines 12A-12D at an end 150 associated with the proximal end 101 and runs within the outer tube 10 from this end 150, parallel to the electrode lines 12A-12D, as is also shown by way of example in FIG. 2. The stub line 15 has a mechanical length s. The sum of the electrode line length L and the stub line length s is preferably such that the effective line length L+s at the electrode line 12A-12D corresponds to a parallel resonance.

The effective line length of the electrode lines 12A-12D is thus modified by the stub line 15 in such a way that at a predetermined MR excitation frequency an in-coupling of fields and therefore heating at the electrode poles 13A to 13D is eliminated. Excess heating at the electrode poles 13A to 13D may be avoided in this way.

A stub line 15 (as shown in FIG. 1) may be arranged at the proximal end 101 and/or at the distal end 100. Here, it is also conceivable and possible to provide a stub line 15 at each of both the proximal end 101 and also the distal end 100.

The arrangement of the stub line 15 at the proximal end 101 or at the distal end 100 may also be dependent on the use. For example, a stub line 15 at the proximal end 101 may be particularly effective for neuro-stimulation, whereas a stub line 15 in the region of the distal end 100 may be advantageous for an application as a heart electrode.

In principle, each electrode line 12A-12D may be connected to a separate stub line 15 so that the effective line length of each electrode line 12A-12D is modified separately.

Figure 4:
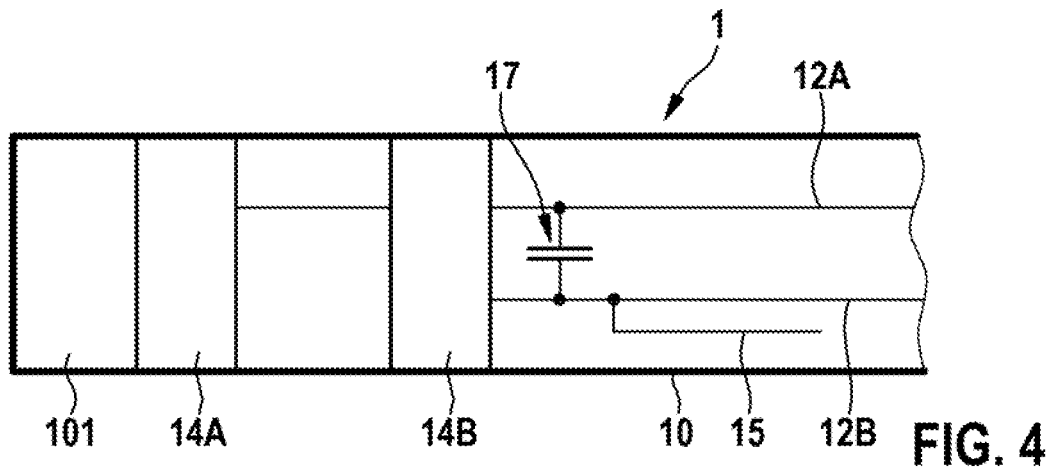
FIG. 4 shows a schematic view of an electrode in the region of a proximal end.
Figure 5:
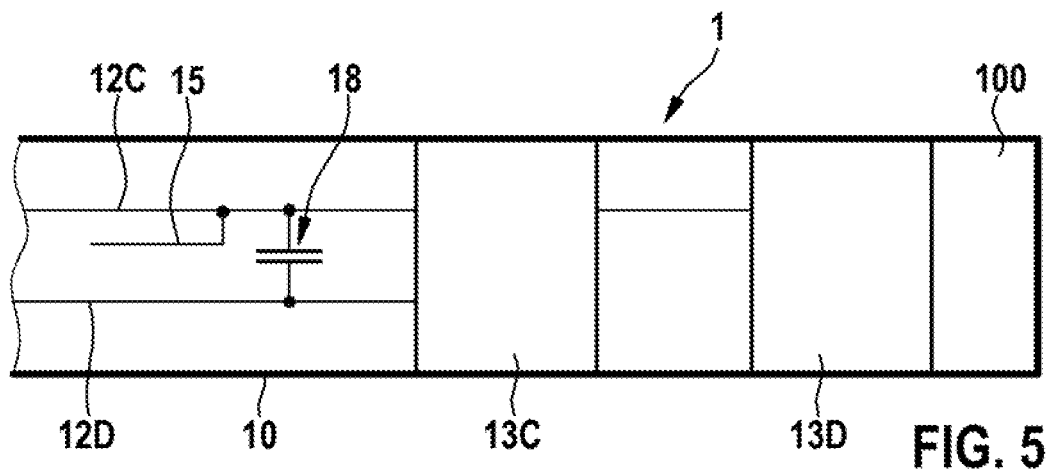
FIG. 5 shows a schematic view of an electrode in tire region of a distal end.

In an advantageous embodiment, the electrode lines 12A-12D, however, are modified with respect to their effective line length via a (single) common stub line 15. The electrode lines 12A-12D, at the particular end 100, 101 at which the stub line 15 is arranged, to this end may be electrically short-circuited at the MR excitation frequency for which the electrode 1 is to be optimized by providing capacitors between the electrode lines 12A-12D, as is shown schematically in FIGS. 4 and 5. Adjacent electrode lines 12A, 12B at the proximal end 101 may thus be electrically short-circuited at the MR excitation frequency via a capacitor 17 arranged in between, for example, in the form of a separate capacitor element (FIG. 4). Additionally or alternatively, adjacent electrode lines 12C, 12D may be short-circuited in the region of the distal end 100 via a capacitor arranged in between in the form, for example, of a capacitor element 18 (FIG. 5). Accordingly, all electrode lines 12A-12D may be effectively short-circuited with one another so that a single stub line 15, as shown by way of example in FIGS. 4 and 5, is suitable in order to modify the effective line length at all electrode lines 12A-12D.

Figure 6:
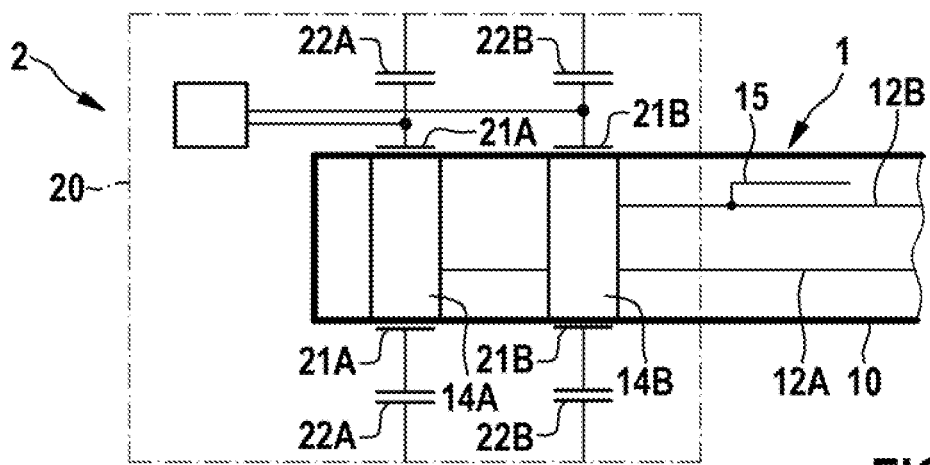
FIG. 6 shows a schematic view of an electrode in conjunction with an active device.

An effective short circuit at the MR excitation frequency, for example, at 64 MHz or 123 MHz, may also be brought about via the active device 2. The electrode 1 thus contacts associated electrical contact elements of the active device 2 via its connection elements 14A-14D, as is shown by way of example in FIG. 6 for two connection elements 14A, 14B and associated electrical contact elements 21A, 21B of the active device 2. The electrical contact elements 21A, 21B, each configured, for example, as a bushing to make electrical contact with tire associated sleeve-shaped connection elements 14A, 14B of the electrode 1, may each be short-circuited here with respect to a housing 20 of the active device 2 at the MR excitation frequency via a capacitor in the form of a capacitor element 22A, 22B, such that an effective short circuit for the electrode lines 12A-12D is caused within the active device 2. In this case a stub line 15 connected at the proximal end 101 to one of the electrode lines 12A-12D is effective for modifying the electrical length of ail electrode lines 12A-12D.

In the exemplary embodiment of the electrode 1 shown in FIG. 1, the stub line 15 runs parallel to the electrode lines 12A-12D within the outer tube 10 and is connected via its end 150 to an associated electrode line 12A-12D, and by contrast is free (electrically open) at its other end.

In an exemplary embodiment shown in FIG. 7, the stub line 15 by contrast firstly runs starting from its end 150, at which the stub line 15 is connected to one of the electrode lines 12A-12D, away from the proximal end 101, parallel 10 the electrode lines 12A-12D. At a turning point 151 the direction of extent of the stub line 15 reverses, however, so that the stub line 15 runs with a portion back in the direction of the proximal end 101. The portions may have portion lengths S1, S2 which modify the effective line length of the electrode lines 12A-12D in such a way that the effective line length corresponds to a parallel resonance of higher order (for example, the next-higher parallel resonance in FIG. 3 at a length of approximately 150 cm for the MR excitation frequency of 64 MHz (1.5 Tesla)).

In an exemplary embodiment shown in FIG. 8, the stub line 15 is wound helically and runs within the outer tube 10 around the electrode lines 12A-12D. The stub line 15 is connected via its end 150 to an associated electrode line 12A-12D. The stub line 15 here has a mechanical length s.

Figure 9A:
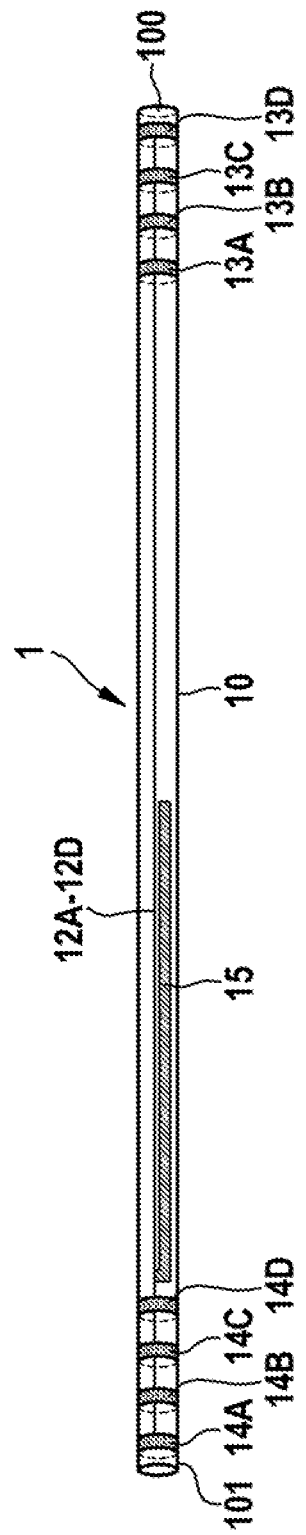
FIG. 9A shows a view of another exemplary embodiment of an electrode with a stub line.
Figure 9B:
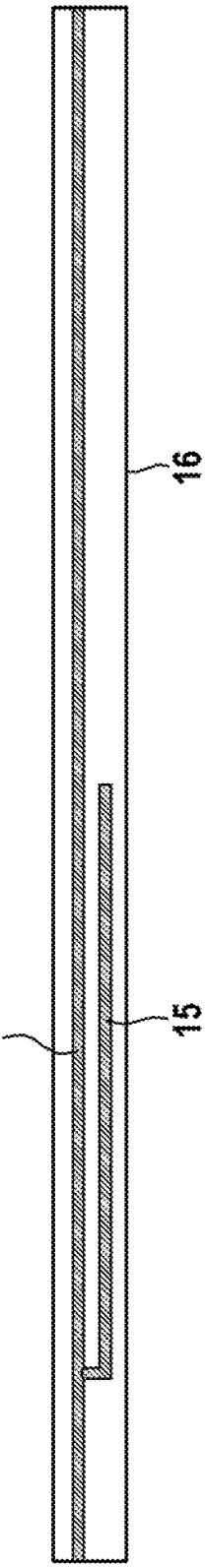
FIG. 9B show s a separate view of the stub line on an associated electrode line.

In an exemplary embodiment shown in FIGS. 9A and 9B, the stub line 15 is arranged as a flexible conductive track on a support 16, wherein in the case of FIG. 9A the associated electrode line 12A is formed as described above. In addition, the stub line 15 together with the electrode line 12A, for example, may be printed onto the support 16, as is shown in FIG. 9B. The support 16 may be formed, for example, by a flexible film material and is manufactured from an electrically insulating material, for example, an LCP material.

In the exemplary embodiment according to FIGS. 9A and 9B, the stub line 15 runs in a straight line parallel to the associated electrode line 12A. By contrast, in the exemplary embodiment according to FIGS. 10A and 10B, the stub line 15, which is again manufactured as a flexible conductive track on a flexible support 16, is arranged in a coiled fashion in the outer tube 10 in that a portion 160 of the support 16 carrying the stub line 15, which portion is branched off from a portion 161 carrying the electrode line 12A, is laid and received in a coiled fashion within the outer tube 10.

Figure 11A:
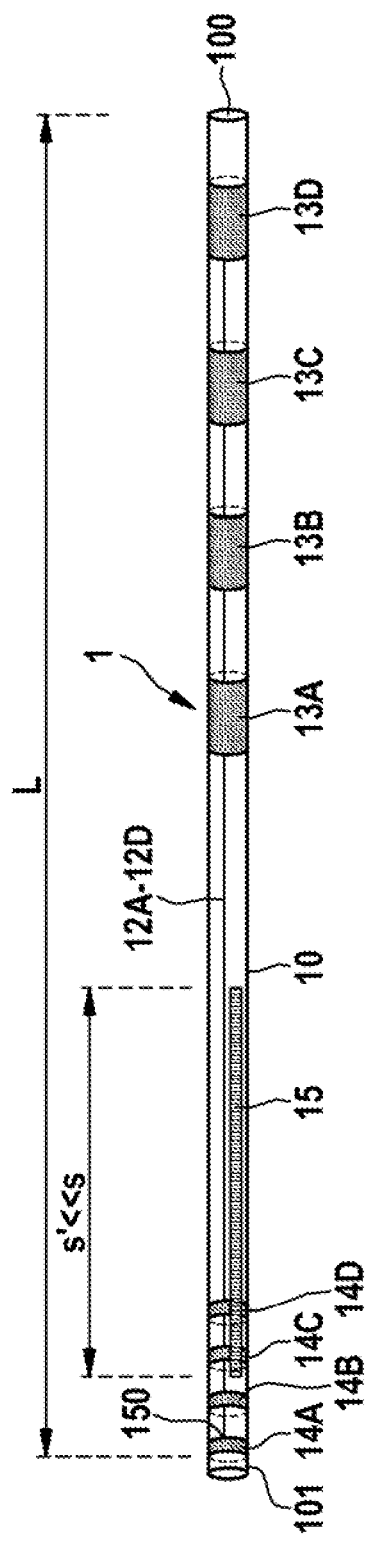
FIG. 11A shows a view of another exemplary embodiment of an electrode with a stub line.
Figure 11B:
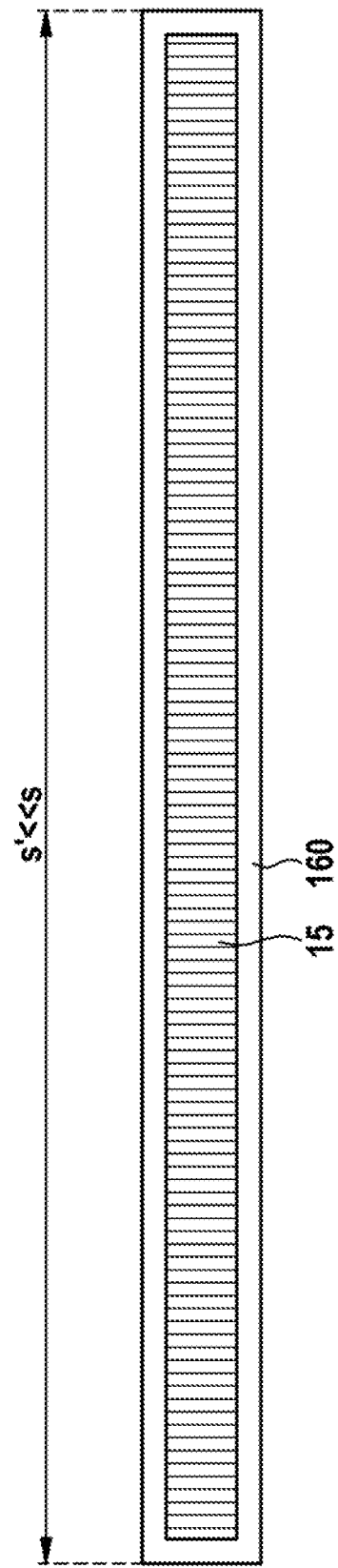
FIG. 11B shows a separate view of die stub line.
Figure 11C:
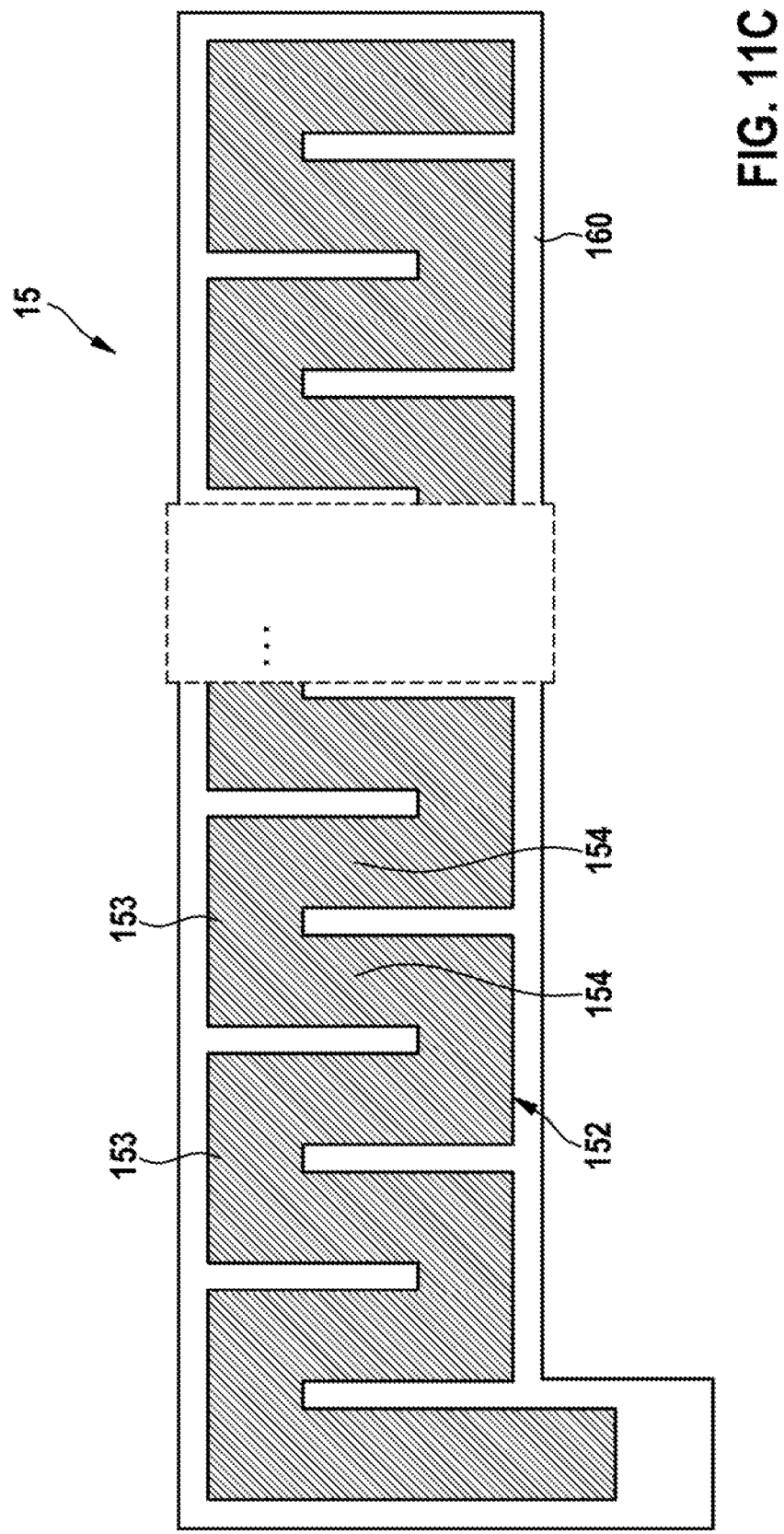
FIG. 11C shows an enlarged depiction of the stub line.

In an exemplary embodiment shown in FIGS. 11A to 11C, the stub line 15 is formed in a meandering fashion and, for example, is realized by a flexible conductive track printed on a support portion 160. Here, the stub line 15 is formed by meander portions 152 arranged side-by-side, each formed by longitudinal portions 153 and transverse portions 154 arranged in alternation, and runs parallel to the electrode lines 12A-12D within the outer tube 10. The stub line 15 is connected via its end 150 to an associated electrode line 12A-12D. Due to the meandering form, the required length s' of the stub line 15 along the support portion 160 is much shorter than the actual geometric length S of the stub line 15 along the turns of the meander.

Figure 12:
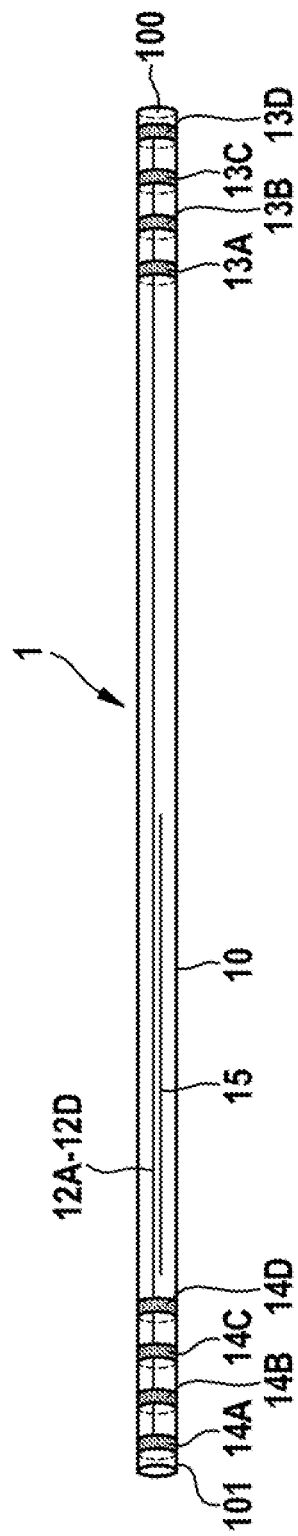
FIG. 12 show s a view of another exemplary embodiment of an electrode with a stub line.
Figure 13:
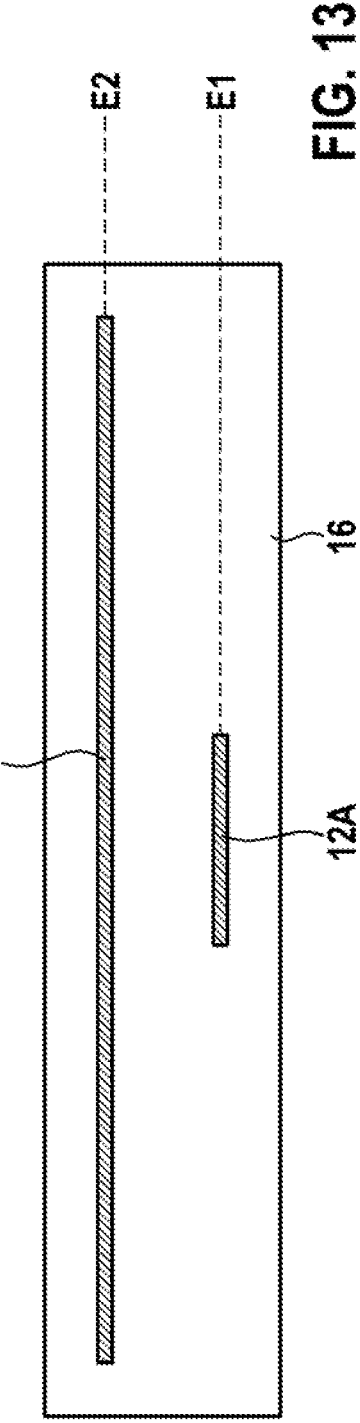
FIG. 13 shows a schematic view of a stub line and an associated electrode line on a support.

In an exemplary embodiment shown in FIGS. 12 and 13, the stub line 15 runs in a straight line within the outer tube 10, wherein in this exemplary embodiment the stub line 15 and an associated electrode line 12A are embedded in a support 16 and run within the support 16 along parallel planes E1, E2. Here, the stub line 15 may have a meandering form (similar to FIGS. 11A to 11C). The support 16 and the conductive tracks embedded therein may each be flexible. The support 16, for example, may have a thickness in the range between 10 μm and 100 μm, for example, 50 μm, and a width between 0.5 mm and 1.5 mm, for example, 1 mm.

The concept forming the basis of the present invention is not limited to the exemplary embodiments described above, and may also be realized in other embodiments.

An electrode of the kind described here may in principle be used in completely different applications, in each case with associated active devices, for example, implantable active devices or also active devices that are to be used externally of the patient.

Such an electrode may have one or more electrode lines and a corresponding number of electrode poles and connection elements. The electrode poles may also be configured in a form other than as ring electrode poles.

It will be apparent to those skilled in the art that numerous modifications and variations of the described examples and embodiments are possible in light of the above teachings of the disclosure. The disclosed examples and embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMBERS/SIGNS 1 implantable electrode
10 outer tube
100 distal end
101 proximal end
11 inner tube
12, 12A-D electrode line
120 conductor
121 insulation
13A-D electrode pole
14A-D connection element
15 stub line
150 end
151 turning point
152 meander portions
153 length portions
154 transverse portions
16 support
160, 161 support portion
17 capacitor (capacitor element)
18 capacitor (capacitor element)
2 active device
20 housing
21A, 21B electrical contact element
22A, 22B capacitor (capacitor element)
E1, E2 plane
G tissue
L electrode line length
s stub line length
s1, s2 portion length

We claim:

1. An implantable electrode lead, comprising: an outer tube, at least one electrode line, at least one electrode pole, and a stub line; wherein:
   the implantable electrode lead has an elongate structure;
   the outer tube, having a distal end and a proximal end, wherein the implantable electrode lead is connectable in a region of the proximal end to an active device;
   the at least one electrode line is arranged in the outer tube;
   the at least one electrode pole is arranged in a region of the distal end and is electrically connected to the at least one electrode line, for electrically contacting tissue surrounding the implantable electrode lead when the implantable electrode lead is in an implanted state; and
   the stub line is connected in the region of the distal end or the region of the proximal end of the outer tube to the at least one electrode line in order to extend an effective line length of the at least one electrode line, the stub line extending along a length of the outer tube in parallel with the at least one electrode line, wherein the stub line includes first and second ends, wherein only the first end of the stub line is electrically connected to the at least one electrode line along a length of the at least one electrode line, and the second end of the stub line is opposite the first end and is a free end which is unconnected to any element.

2. The implantable electrode lead according to claim 1, wherein the at least one electrode line has a mechanical electrode line length and the stub line has a mechanical stub line length, wherein the effective line length of the at least one electrode line is given from is given from a sum of the line length and the stub line length.

3. The implantable electrode lead according to claim 2, wherein the sum of the electrode line length and the stub line length is selected such that the at least one electrode line has a resultant effective line length corresponding to a predetermined MR excitation frequency of a parallel resonance.

4. The implantable electrode lead according to claim 1, wherein the stub line runs in a straight line, helically, or in a meandering fashion.

5. The implantable electrode lead according to claim 1, wherein the stub line is formed by a flexible conductive track.

6. The implantable electrode lead according to claim 1, wherein the stub line is arranged jointly with the at least one electrode line on a support.

7. The implantable electrode lead according to claim 6, wherein the stub line and the at least one electrode line are formed by conductive tracks on the support running parallel to one another along different planes.

8. The implantable electrode lead according to claim 1, wherein the at least one electrode line comprises a plurality of electrode lines, and the at least one electrode pole comprises a plurality of electrode poles arranged in the region of the distal end, wherein each electrode line is electrically connected to one of the electrode poles.

9. The implantable electrode lead according to claim 8, wherein precisely one stub line is electrically connected at the distal end or at the proximal end to the plurality of electrode lines.

10. The implantable electrode lead according to claim 8, wherein the plurality of electrode lines is electrically short-circuited in the region of the distal end and/or in the region of the proximal end at a predetermined MR excitation frequency.

11. The implantable electrode lead according to claim 10, wherein the plurality of electrode lines in the region of the distal end and/or in the region of the proximal end is electrically connected to one another via at least one capacitor.

12. The implantable electrode lead according to claim 1, wherein at least one connection element arranged in the region of the proximal end and electrically connected to the at least one electrode line for making electrical contact with the active device.

13. The implantable electrode lead according to claim 1, wherein the at least one electrode pole is designed for stimulation of the spinal cord.

14. A system comprising an active device and the implantable electrode lead according to claim 1 connected to the active device.

15. The system according to claim 14, wherein the active device has a housing and at least one electrical contact element for making electrical contact with the at least one electrode line of the implantable electrode lead, wherein the at least one electrical contact element is electrically short-circuited to the housing at a predetermined MR excitation frequency.

16. An implantable electrode lead, comprising:
   an outer tube, at least one electrode line, at least one electrode pole, and a stub line;
   wherein:
      the implantable electrode lead has an elongate structure;
      the outer tube, having a distal end and a proximal end, wherein the implantable electrode lead is connectable in a region of the proximal end to an active device;
      the at least one electrode is line arranged in the outer tube extending from the proximal end to the distal end;
      the at least one electrode pole is arranged in a region of the distal end and is electrically connected to the at least one electrode line, for electrically contacting tissue surrounding the implantable electrode lead when the implantable electrode lead is in an implanted state; and
      the stub line is arranged in the outer tube and is connected in the region of the distal end or the region of the proximal end to the at least one electrode line in order to extend an effective line length of the at least one electrode line,
   wherein the stub line has a mechanical stub line length that extends along a length of the outer tube in parallel with the at least one electrode line;
   wherein the stub line includes first and second ends, wherein only the first end of the stub line is electrically connected to the at least one electrode line along a length of the at least one electrode line, and the second end of the stub line is opposite the first end and is a free end which is unconnected to any element.

17. The implantable electrode lead according to claim 16, wherein the at least one electrode line has a mechanical electrode line length, wherein the effective line length of the at least one electrode line is given from a sum of the electrode line length and the stub line length.

18. The implantable electrode lead according to claim 17, wherein the sum of the electrode line length and the stub line length is selected such that the at least one electrode line has a resultant effective line length corresponding to a predetermined MR excitation frequency of a parallel resonance.

19. The implantable electrode lead according to claim 16, wherein the stub line is formed by a flexible conductive track.

20. The implantable electrode lead according to claim 16, wherein the stub line is arranged jointly with the at least one electrode line on a support.

* * * * *